(12) United States Patent
Mousa (10) Patent No.: US 10,993,909 B1
(45) Date of Patent: May 4, 2021

(54) METHOD AND COMPOSITION FOR TREATING UPPER RESPIRATORY TRACT INFLAMMATORY AND INFECTIOUS DISEASES

(71) Applicant: Virothera Pharmaceuticals LLC, Wynantskill, NY (US)

(72) Inventor: Shaker A. Mousa, Wynantskill, NY (US)

(73) Assignee: Virothera Pharmaceuticals LLC, Wynantskill, NY (US)

( * ) Notice: Subject to any disclaimer, the term of this patent is extended or adjusted under 35 U.S.C. 154(b) by 0 days.

(21) Appl. No.: 16/906,043

(22) Filed: Jun. 19, 2020

Related U.S. Application Data (60) Provisional application No. 62/992,867, filed on Mar. 20, 2020.

(51) Int. Cl.
| | | |
|---|---|---|
| *A61K 9/00* | (2006.01) | |
| *A61K 9/51* | (2006.01) | |
| *A61K 9/48* | (2006.01) | |
| *A61K 31/4706* | (2006.01) | |
| *A61K 31/167* | (2006.01) | |
| *A61K 31/4965* | (2006.01) | |
| *A61K 33/30* | (2006.01) | |
| *A61K 31/727* | (2006.01) | |
| *A61K 31/573* | (2006.01) | |
| *A61K 47/06* | (2006.01) | |
| *A61K 9/10* | (2006.01) | |
| *A61K 9/08* | (2006.01) | |
| *A61K 47/32* | (2006.01) | |
| *A61K 47/02* | (2006.01) | |
| *A61K 9/50* | (2006.01) | |

(52) U.S. Cl.
CPC ............ *A61K 9/0078* (2013.01); *A61K 9/008* (2013.01); *A61K 9/0073* (2013.01); *A61K 9/08* (2013.01); *A61K 9/10* (2013.01); *A61K 9/4866* (2013.01); *A61K 9/5015* (2013.01); *A61K 9/5123* (2013.01); *A61K 9/5138* (2013.01); *A61K 31/167* (2013.01); *A61K 31/4706* (2013.01); *A61K 31/4965* (2013.01); *A61K 31/573* (2013.01); *A61K 31/727* (2013.01); *A61K 33/30* (2013.01); *A61K 47/02* (2013.01); *A61K 47/06* (2013.01); *A61K 47/32* (2013.01)

(58) Field of Classification Search
CPC .......................... A61K 9/5161; Y10S 977/773
See application file for complete search history.

(56) References Cited

U.S. PATENT DOCUMENTS

| | | | | |
|---|---|---|---|---|
| 2006/0216353 | A1* | 9/2006 | Liversidge | A61K 9/008 424/489 |
| 2011/0224312 | A1* | 9/2011 | Da Rocha | A61K 9/0075 514/785 |
| 2017/0189529 | A1* | 7/2017 | Estelles | C07K 16/1018 |

FOREIGN PATENT DOCUMENTS

| | | | | |
|---|---|---|---|---|
| CN | 1917859 A | * | 2/2007 | ........... A61K 31/122 |

OTHER PUBLICATIONS

Wu et al (Molecular Pharmaceutics, 2016, vol. 13, pp. 3279-3291). (Year: 2016).*
Sperber et al (Clinical Therapeutics, 1995, vol. 17, pp. 622-636). (Year: 1995).*
Shetty et al (International Journal of Pharm, 2018, vol. 544, pp. 222-234). (Year: 2018).*
CN-1917859-A, Espacenet English translation, downloaded Sep. 2020 (Year: 2020).*
Ghiasi et al., A Pilot Study of Nebulized Heparin for Prevention of Ventilator Induced Lung Injury: Comparative Effects with an Inhaled Corticosteroid, Indian J Crit. Care Med. Oct. 2017; 21(10): 634-639, 13 pages.
Bai et al, Inhalable Lactose-Based Dry Powder Formulations of Low Molecular Weight Heparin, J. Aerosol Medicine and Pulmonary Drug Delivery, vol. 23, No. 2, 2010, 97-104, 8 pages.
Godugu et al., Effect of Sulfated Non-Anticoagulant Low Molecular Weight Heparin in Cancer and Non-Cancer Associated Thrombosis, Blood (2019) 134 (Supplement_1): 3670. https://doi.org/10.1182/blood-2019-130992, 2 pages.
Tang et al., Anticoagulant treatment is associated with decreased mortality in severe coronavirus disease 2019 patients with coagulopathy, J Thromb Haemost. Mar. 27, 2020. doi: 10.1111/jth.14817, 15 pages.
Kollias et al., Thromboembolic risk and anticoagulant therapy in Covid-19 patients: Emerging evidence and call for action, Br J Haematol. Apr. 18, 2020. doi: 0.1111/bjh.16727. [Epub ahead of print], 2 pages.

(Continued)

*Primary Examiner* — Mark V Stevens
(74) *Attorney, Agent, or Firm* — Schmeiser, Olsen & Watts, LLP (57) ABSTRACT

A composition and method for treating a mammal infected with a virus therein, and an inhalation delivery system for prevention and treatment of upper respiratory tract viruses, by administering a therapeutic dose of the composition to the mammal. The composition includes:
microparticles and/or nanoparticles, wherein a pharmaceutically active agent, corticosteroid and/or hydroxychloroquine, niclosamide, and/or favipiravir, and a zinc salt are incorporated in the microparticles and/or nanoparticles. The pharmaceutically active agent is unfractionated heparin (UFH), Low Molecular Weight Heparin (LMWH), sulfated non-anticoagulant heparin (S-NACH), other glycosaminoglycans (GAGs), or combinations thereof.

30 Claims, 3 Drawing Sheets

(56) References Cited

OTHER PUBLICATIONS

Qi, et al, Delivery of therapeutic levels of heparin and low molecular weight heparin through pulmonary route, PNAS 101 (26): 9867-9872, Apr. 28, 2004, 6 pages.
Dr Peter T. Daley-Yates, Inhaled corticosteroids potency, dose equivalence and and therapeutic index. Br J Clin Pharmacology 80:3, 372-378, published Mar. 24, 2015. 9 pages.
Lan et al., Positive RT-PCR Test Results in Patients Recovered From Covid-19, JAMA. Feb. 27, 2020. doi: 10.1001/jama.2020.2783. 2 pages.
Savarino et al., Effects of chloroquine on viral infections: an old drug against today's diseases?, Lancet Infect Dis 2003; 3: 722-27, 7 pages.
Lechanteur et al., Influence of Composition and Spray-Drying Process Parameters on Carrier-Free DPI Properties and Behaviors in the Lung: A review, Pharmaceutics 2020, 12, 55; doi:10.3390/pharmaceutics12010055, 21 pages.
Sapp et al., Guidance on Minimizing Risk of Drug-Induced Ventricular Arrhythmia During Treatment of Covid-19: A Statement from the Canadian Heart Rhythm Society, Canadian Journal of Cardiology (2020), doi: https://doi.org/10.1016/j.cjca.2020.04.003, 19 pages.
U.S. Appl. No. 62/992,867, filed Mar. 20, 2020, Conf No. 6438.
Dong et al., Discovering drugs to treat coronavirus disease 2019 (Covid-19), Drug Discov Ther. 2020;14(1):58-60. doi: 10.5582/ddt.2020.01012, 1 page.
Touret et al., Of chloroquine and Covid-19, Antiviral Res. Mar. 5, 2020;177:104762. doi: 10.1016/j.antiviral.2020.104762. [Epub ahead of print] Review, 1 page.
Zhang et al., Clinical Trial Analysis of 2019-nCoV Therapy Registered in China, J Med Virol. Feb. 28, 2020, doi:. 10.1002/jmv.25733. [Epub ahead of print], 2 pages.
Gao et al., Breakthrough: Chloroquine phosphate has shown apparent efficacy in treatment of Covid-19 associated pneumonia in clinical studies, Biosci Trends. Mar. 16, 2020;14(1):72-73. doi: 10.5582/bst.2020.01047. Epub Feb. 19, 2020, 1 page.
Colson et al., Chloroquine for the 2019 novel coronavirus SARS-CoV-2, Int J Antimicrob Agents. Mar. 2020;55(3):105923. doi: 0.1016/j.ijantimicag.2020.105923. Epub Feb. 15, 2020, 1 page.
Xu et al., Broad Spectrum Antiviral Agent Niclosamide and its Therapeutic Potential, ACS Infect. Dis. 2020, 6, 5, 909-915, Mar. 3, 2020, 7 pages.
U.S. Appl. No. 16/905,986, filed Jun. 19, 2020, Conf. No. 1069.
Gautret et al., Hydroxychloroquine and azithromycin as a treatment of Covid-19: results of an open-label non-clinical trial, International Journal of Antimicrobial Agents (2020), doi: https://doi.org/10.1016/j.jantimicag.2020.105949, 25 pages.

* cited by examiner

Atomization
Define target particle size
$f$ (geometry, pressure)

Drying Conditions
- Product morphology
- Water content

Spray Solution
Stability versus process time
Shear, pH, concentration, interactions Drying nitrogen

Collection Efficiency
High Value Product
$f$ (geometry, product properties)

Cyclone

Atomizer

Drying Chamber

Hot drying gas contacts droplet

Droplet Surface
Spray Solution
Droplet
Surface-active excipients

Engineered Dry Powder Particles

| | |
|---|---|
| Neat API | Single Solvent Solution |
| Amorphous API/Excipient | Single Co-Solvent Solution |
| Crystalline API/Excipient | Single, Dual, or Variable Process Settings – Solution or Suspension |
| Mixed Approaches | Single, Dual, or Variable Process Settings – Solution or Suspension |

FIG. 3

METHOD AND COMPOSITION FOR TREATING UPPER RESPIRATORY TRACT INFLAMMATORY AND INFECTIOUS DISEASES

RELATED APPLICATIONS

The present invention claims priority to U.S. Provisional No. 62/992,867, filed on Mar. 20, 2020, which is incorporated herein by reference in its entirety.

TECHNICAL FIELD

This invention pertains to methods and compositions for treating upper respiratory tract inflammatory, infectious diseases, and associated complications.

BACKGROUND

Novel coronavirus (2019-nCoV) or the severe acute respiratory syndrome coronavirus 2 (SARS-CoV-2) emerged in year 2019. The coronavirus originated in bats and was transmitted to humans through yet unknown intermediary animals in Wuhan, Hubei province, China in December 2019. As of March 2020, about 96,000 cases of coronavirus disease 2019 (COVID-2019) have been reported and over 3300 deaths have been reported. The coronavirus disease is transmitted by inhalation or contact with infected droplets and the incubation period ranges from 2 to 14 days. Typical symptoms of coronavirus disease include, but are not limited to, fever, cough, sore throat, breathlessness, and fatigue. Although the coronavirus disease is mild in most people, in others (usually the elderly and those with comorbidities and weak immune systems), the coronavirus disease may progress to pneumonia, acute respiratory distress syndrome (ARDS) and multi organ dysfunction. However, many people who are infected the coronavirus disease are asymptomatic. Studies have shown that heparin or Low Molecular Weight Heparins (LMWH) had anti-inflammatory properties, anti-thrombotic, anti-complement, and a direct antiviral action, due to its ability to prevent SARS-CoV-2 virus entry into host cells. These activities, together with its anticoagulant action, could explain the ability of heparin to ameliorate COVID-19 clinical course. However, its systemic use by intravenous or subcutaneous injection is associated with adverse bleeding side effects.

BRIEF SUMMARY

The present invention provides a composition, comprising: microparticles and/or nanoparticles, wherein a pharmaceutically active agent, corticosteroid and/or hydroxychloroquine and/or favipiravir, and a zinc salt are incorporated in the microparticles and/or nanoparticles. The pharmaceutically active agent is selected from the group consisting of unfractionated heparin (UFH), Low Molecular Weight Heparin (LMWH), sulfated non-anticoagulant heparin (S-NACH), other glycosaminoglycans (GAGs), and combinations thereof.

The present invention provides a method for treating a mammal infected with a virus, the method comprising: administering a therapeutic dose of the composition to a mammal.

The present invention provides inhalation delivery system for prevention and treatment of upper respiratory tract viruses. The inhalation delivery system comprises an apparatus configured to deliver a therapeutic dose of the composition to a mammal via inhalation delivery.

DETAILED DESCRIPTION

The present invention provides a therapeutic formulation/composition for treating and/or mitigating viral-mediated infectious disease, including coronavirus disease, in a person, utilizing nebulization, dry powder inhaler (DPI), metered-dose inhaler (MDI), nasal spray, and/or aerosolized propellant/inhaler. Hydrofluoroalkane (HFA) may be used for pressurizing heparins (including unfractionated heparin, low molecular weight heparins, sulfated non-anticoagulant heparin), corticosteroid and/or hydroxychloroquine, favipiravir along with zinc salt. Excipients and stabilizers in the formulation might include lactose, mannitol, trehalose and raffinose as well as other excipients. Pulmonary or nasal delivery of the formulation provides anti-inflammatory, anti-thrombotic and anti-viral effects that mitigate the multifaceted disorders and complications in viral-mediated infectious diseases including coronavirus.

The MDI contains a suspension or a solution of micronized polar drug particles in either one nonpolar propellant or a mixture of two or three nonpolar propellants. The nonpolar propellants are chosen to achieve desired vapor pressure and spray characteristics. In suspension formulations, particle agglomeration is reduced by the addition of a surfactant such as sorbitan trioleate, lecithin, or oleic acid. The surfactant may contribute to a characteristic taste of the aerosol.

A hardware component of the MDI is a metering valve, which delivers a known quantity of propellant containing the micronized drug, surfactant, and any other excipients with each actuation. Following release by an actuator, volatilization of the HFA propellant breaks up the liquid propellant, resulting in a high-velocity plume that is expelled 20-30 cm into free air. As a result, a large portion, up to 90 percent, of the aerosolized drug may be deposited in the oropharynx of the person.

Some DPIs use gelatin capsules that contain either micronized drug mixed with a lactose or glucose carrier, or micronized drug pelletized or spheronized into visible agglomerates. A carrier or spheronization may be used because of a cohesiveness of pure micronized drug, making filling and emptying of gelatin capsules and bulk-reservoir DPIs inefficient. Once inhaled, the drug particles separate from the carrier or are deagglomerated by the inspired (i.e., inhaled) airflow.

A problem associated with use of a DPIs is that the DPI relies on the patient's inspiratory effort to enable the drug to reach the lung. If inhalation of a drug is not performed at an optimal inspiratory flow rate for a particular DPI device, delivery of the drug to the lung will be reduced or negated, because the dose of drug emitted or dispensed is decreased and the particle size of the powder aerosol is increased. Many young children as well as older children and adults with severe bronchospasm cannot generate sufficient inspiratory flow to get the most benefit from a DPI, an MDI, a nebulizer, or a nasal spray.

Particle generation and characterization pertaining to use of a DPI for the formulation of the present invention include generation of fine particles using conventional methods, such as jet milling, micronization and spray drying. Particle characterizations include particle size analysis using laser diffraction and microscopy and/or polymorphism evaluation.

Dosage of the formulation of the present invention may be arrived at or determined form selection and product performance testing of candidate formulations. Formulation selection and optimization are aided by statistical experimental design. Studies impacting dosage of formulations are facilitated by on-site filling equipment and stability chambers.

Devices and components commonly evaluated for the formulation of the present invention include MDIs (valves, cans, and actuators) and DPIs (blister packaging, device durability, and reliability). Analytical testing, method development, validation, and testing services support all phases of product development pertaining to the inventive formulation of the present invention, from feasibility through regulatory submission and post-approval support. Full product release and stability testing services are available.

Inhalation injury (IHI) using ventilators or intubation causes significant morbidity and mortality due to both local and systemic effects. Nebulized heparin promotes improvement in lung function and decreased mortality in IHI by reducing the inflammatory response and fibrin cast formation. The study objective was to determine if nebulized heparin 10,000 units improves lung function and decreases mechanical ventilation duration, mortality, and hospitalization length in IHI with minimal systemic adverse events. This retrospective, case-control study evaluated efficacy and safety of nebulized heparin administered to mechanically ventilated adults admitted within 48 hours of confirmed IHI (Ghiasi F. et al, A Pilot Study of Nebulized Heparin for Prevention of Ventilator Induced Lung Injury: Comparative Effects with an Inhaled Corticosteroid, Indian J Crit. Care Med. 2017 October; 21(10): 634-639).

Latest studies have indicated that inhalation of unfractionated heparin (UFH) treats local inflammation, mucus hypersecretion and lung injury, without systemic anticoagulation, and is safe. It was shown that inhaled UFH significantly improves lung function over 21 days of treatment in patients with COPD receiving pulmonary rehabilitation and that UFH provides safe and effective way of treating COPD. This latest study concluded that Inhaled nebulized UFH is safe and provides additional clinical benefit for patients with moderate to very severe COPD through effects that are independent of its anticoagulant activity (Bai S et al., Inhalable Lactose-Based Dry Powder Formulations of Low Molecular Weight Heparin, J. Aerosol Medicine and Pulmonary Drug Delivery, Volume 23, Number 2, 2010, 97-104).

However, antithrombotic activities might be required to combat pro-thrombotic episodes in COPD and infectious upper respiratory tract viral infections such as COVID-19 that lead to high risk deep vein thrombosis (DVT) and pulmonary embolism (PE). Since UFH possesses high plasma protein binding which causes the UHF to be trapped and become unviable for a desired antithrombotic effect, the present invention uses, in one embodiment, FDA approved Low Molecular Weight Heparins (LMWH) or sulfated Non-anticoagulant LMWH (S-NACH), which possess low plasma protein binding and antithrombotic activities without bleeding side effects (Godugu K, Mousa S S, Darwish N E, Mousa S A, Effect of Sulfated NON-Anticoagulant Low Molecular Weight Heparin in Cancer and NON-Cancer Associated Thrombosis, Blood (2019) 134 (Supplement 1): 3670. https://doi.org/10.1182/blood-2019-130992). Additionally, complement activation and inflammation are among the major drivers for the clinical complications in COVID-19. In that regards, it is well-known that heparin and other glycosaminoglycans (GAGs) inhibit complement activation and inflammation, which would impact the severity of COVID-19-associated clinical complications.

The use of anticoagulant therapy with heparin was shown to decrease mortality as well, especially for patients i) who have met the sepsis induced coagulopathy (SIC) criteria >4 (40.0% vs 64.2%, P=0.029) compared to patients with SIC score <4 (29.0% vs 22.6%, P=0.419) or ii) with markedly elevated D-dimer (greater than six-fold at the upper limit of normal) (Tang N, Bai H, Chen X, Gong J, Li D, Sun Z., Anticoagulant treatment is associated with decreased mortality in severe coronavirus disease 2019 patients with coagulopathy, J Thromb Haemost. 2020 Mar. 27. doi: 10.111/jth.14817).

Coagulopathy in corona virus infection has been shown to be associated with high mortality with high D-dimers being a particularly important marker for the coagulopathy (Kollias A, Kyriakoulis K G, Dimakakos E, Poulakou G, Stergiou G S, Syrigos K., Thromboembolic risk and anticoagulant therapy in COVID-19 patients: Emerging evidence and call for action, Br J Haematol. 2020 Apr. 18. doi: 0.1111/bjh.16727. [Epub ahead of print]).

Additionally, the high binding affinity of heparin (nanomolar to sub-nanomolar) to viruses including COVID-19 viruses might be potentially therapeutic for treating COVID-19 viruses. The anti-inflammatory capabilities of heparins, which include downregulation of the NFKB pathway as well as a decrease in levels of inflammatory cytokines such as tumor necrosis factor alpha, interleukin-1-beta, and interleukin-6, independent of heparin's anticoagulant mechanisms, would provide prophylactic and treatment measures of COVID-19.

Inhaled corticosteroids are medicines containing corticosteroids such as beclomethasone, budesonide, ciclesonide, flunisolide, fluticasone, or mometasone in a preparation designed to be inhaled through the mouth. Inhaled corticosteroids act directly in the lungs to inhibit the inflammatory process that causes asthma. However, long-term corticosteroid use is associated with adverse effects. Since heparin works by different mechanisms to modulate inflammatory activity from that of corticosteroid, the present invention uses, in one embodiment, a combination of heparins and lower dose corticosteroid which provides greater benefits and reduced adverse effects. Additionally, in viral infections, heparins have high affinity binding to various viruses.

Severe acute respiratory syndrome-related coronavirus 2 (SARS-CoV-2) has resulted in a pandemic and continues to spread around the globe at an unprecedented rate as of April 2020, with the U.S. having the most cases reported to date. There is no effective therapeutic currently available to fight complications associated with COVID-19. It has recently been discovered that the SARS-CoV-2 spike glycoprotein (SGP) binds to glycosaminoglycans (GAGs), such as heparin with high sub-nanomolar affinity, which is essentially irreversible. This exceptional binding of SARS-CoV-2 SGP with GAGs suggests that heparin, heparin analogs and other GAGs may have effectiveness against COVID-19. Indeed, a sulfated non-anticoagulant heparin (S-NACH) has nearly a same degree of SGP binding, but low molecular weight heparins has reduced SGP binding presumably due to a smaller size and lower sulfation of low molecular weight heparins.

However, use of intravenous and subcutaneously administered heparin does not provide significant distribution into the airways, including the lung, of serious COVID-19 patients. Hence, the present invention overcomes a significant need for pulmonary delivery of heparin and analogs into the lung. There is an urgent need to develop a cGMP-capable route to inhalation heparin with 0.5-5 μm particle sizes, which may be accomplished, in accordance with the present invention, with heparin, LMWH or S-NACH in combination with low dose corticosteroid and/or hydroxychloroquine, favipiravir and with zinc salt. Heparin and/or corticosteroid inhalation and Nasal spray using different corticosteroids could be used at their adjusted doses (Yiwei Q, et al., Delivery of therapeutic levels of heparin and low molecular weight heparin through pulmonary route, PNAS 101 (26): 9867-9872; Daley-Yates P T, Inhaled corticosteroids potency and therapeutic index, Br J Clin Pharmacology 80:3, 372-378). Relevant corticosteroids include beclomethasone, budesonide, ciclesonide, dexamethasone, flunisolide, fluticasone, mometasone, and triamcinolone.

Hydroxychloroquine is approved by the Food and Drug Administration (FDA) for the treatment of malaria, lupus, and rheumatoid arthritis, and as an anti-autoimmune agent. Treatment with hydroxychloroquine, however, is not without risks. Recently, the American Heart Association (AHA), the American College of Cardiology (ACC) and the Heart Rhythm Society (HRS) published a joint statement cautioning clinicians about the potential cardiovascular complications associated with hydroxychloroquine.

Hydroxychloroquine can also block virus infection by increasing endosomal pH required for membrane fusion between the virus and the host cell. Moreover, it was shown to specifically inhibit the replication of SARS-CoV by interfering with the glycosylation of its cellular receptor, ACE2 (Lan, L.; Xu, D.; Ye, G.; Xia, C.; Wang, S.; Li, Y.; Xu, H., Positive RT-PCR Test Results in Patients Recovered From COVID-19, JAMA. 2020 Feb. 27. doi: 10.1001/jama.2020.2783).

In vitro testing revealed an ability of hydroxychloroquine to effectively reduce the viral copy number of SARS-CoV-2. Therefore, several clinical trials were quickly conducted in China, which demonstrated that hydroxychloroquine was to various degree effective in treatment of COVID-19-associated pneumonia. Similarly, in a small open-label non-randomized clinical trial from France, hydroxychloroquine demonstrated positive effect in combination with azithromycin (Savarino, A.; Boelaert, J. R.; Cassone, A.; Majori, G.; Cauda, R., Effects of chloroquine on viral infections: An old drug against today's diseases, Lancet Infect. Dis. 2003, 3, 722-727).

In the wake of the preceding evidence, the U.S. FDA issued an Emergency Use Authorization for the use of hydroxychloroquine to treat COVID-19 in the USA. It is noteworthy that the latest study found no evidence of clinical benefit of the combination of hydroxychloroquine and azithromycin for the treatment of 11 patients with severe COVID-19 (Gautret, P.; Lagier, J.-C.; Parola, P.; Hoang, V T.; Meddeb, L.; Mailhe, M.; Doudier, B.; Courjon, J.; Giordanengo, V.; Vieira, V. E.; et al., Hydroxychloroquine and azithromycin as a treatment of COVID-19: Results of an open-label non-randomized clinical trial, Int. J. Antimicrob. Agents 2020, 105949).

Thus, larger randomized controlled trials are needed for further evaluation of treatment of COVID-19 with hydroxychloroquine. Warning about the cardiac arrhythmia and other safety profiles in COVID-19 patients on oral regimens of chloroquine/hydroxychloroquine limit the potential benefit of chloroquine/hydroxychloroquine in COVID-19 patients (Sapp J L et al., On Minimizing Risk of Drug Induced Ventricular Arrhythmia During Treatment of COVID-19: A Statement from the Canadian Heart Rhythm Society, Can J Cardiol. 2020 Apr. 8. pii: S0828-282X (20)30325-1.), and hence another safer local delivery means is the focus of the present invention in achieving efficacy without adverse effects.

Figure 1:
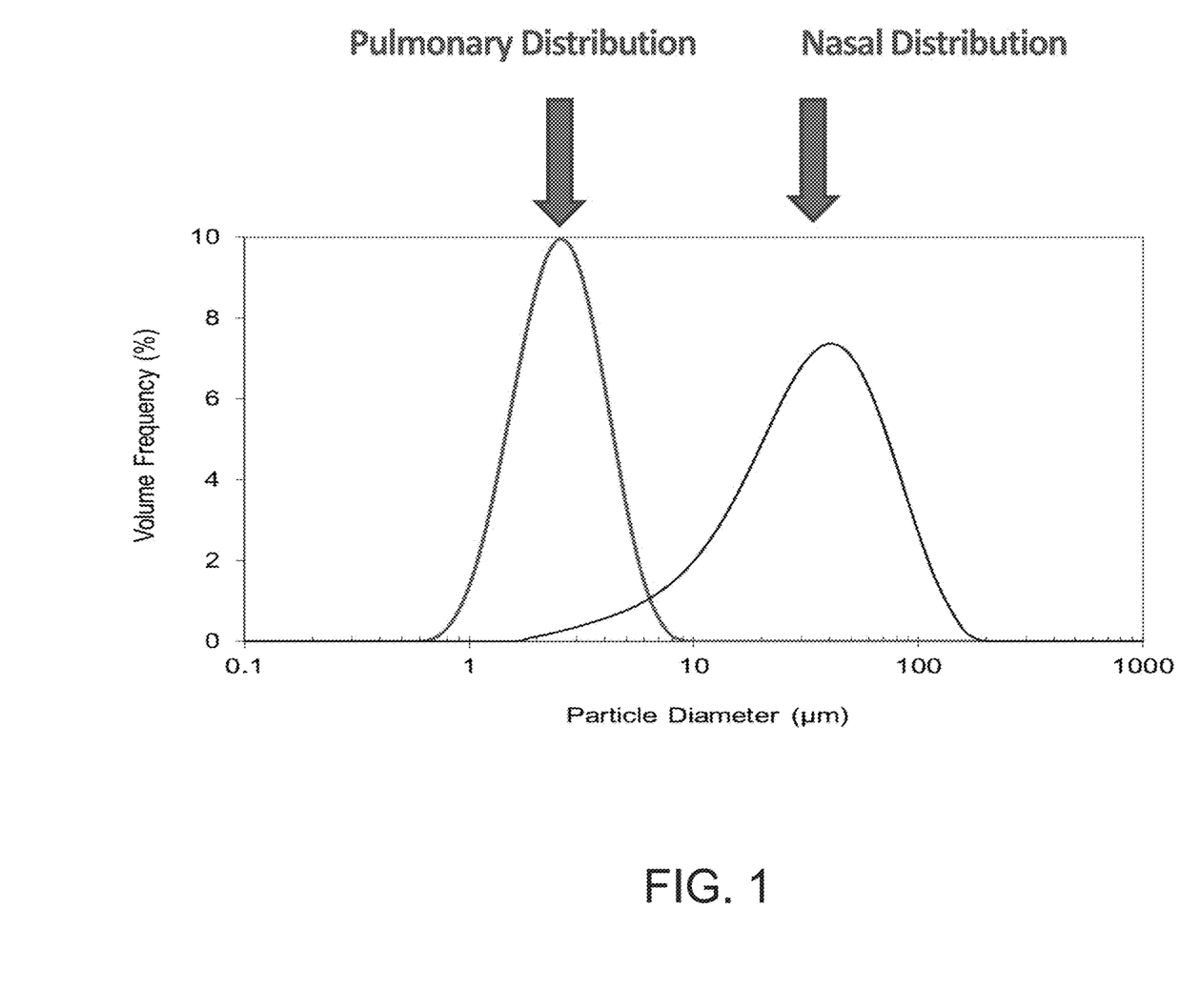
FIG. 1 depicts volume frequency (0%) versus particle diameter (μm) of nanoparticles and microparticles of compositions including one or more pharmaceutically active agents and added zinc salt, using spray drying and/or micronization for inhalation and nasal delivery of the different antiviral compositions to a human subject, in accordance with embodiments of the present invention.

FIG. 1 depicts volume frequency (%) versus particle diameter (μm) of nanoparticles and microparticles of compositions including one or more pharmaceutically active agents and added zinc salt, using spray drying and/or micronization for inhalation and nasal delivery of the different antiviral compositions to a human subject, in accordance with embodiments of the present invention. The inhalation delivery is in accordance with a pulmonary distribution of microparticles as shown. The nasal delivery is in accordance with a nasal distribution of microparticles as shown. The nasal delivery may be via use of a using a nasal spray. The volume frequency amount (by volume) delivered within the subject is a percent of the total antiviral composition inhalation and nasal intake by the human subject. The average size of the microparticles ranged from 0.5-5 μm for pulmonary delivery and from 10-50 μm for nasal delivery. The range of microparticles sizes (i.e., diameters) that can be delivered is support of the pulmonary distribution is 1 to 10 μm. The range of microparticle sizes that can be delivered in support of the pulmonary distribution is 1 to 10 μm. The range of microparticle sizes that can be delivered in support of the nasal distribution is 10 to 100 μm. The antiviral compositions with added zinc salt are described in conjunction with FIG. 2.

Figure 2:
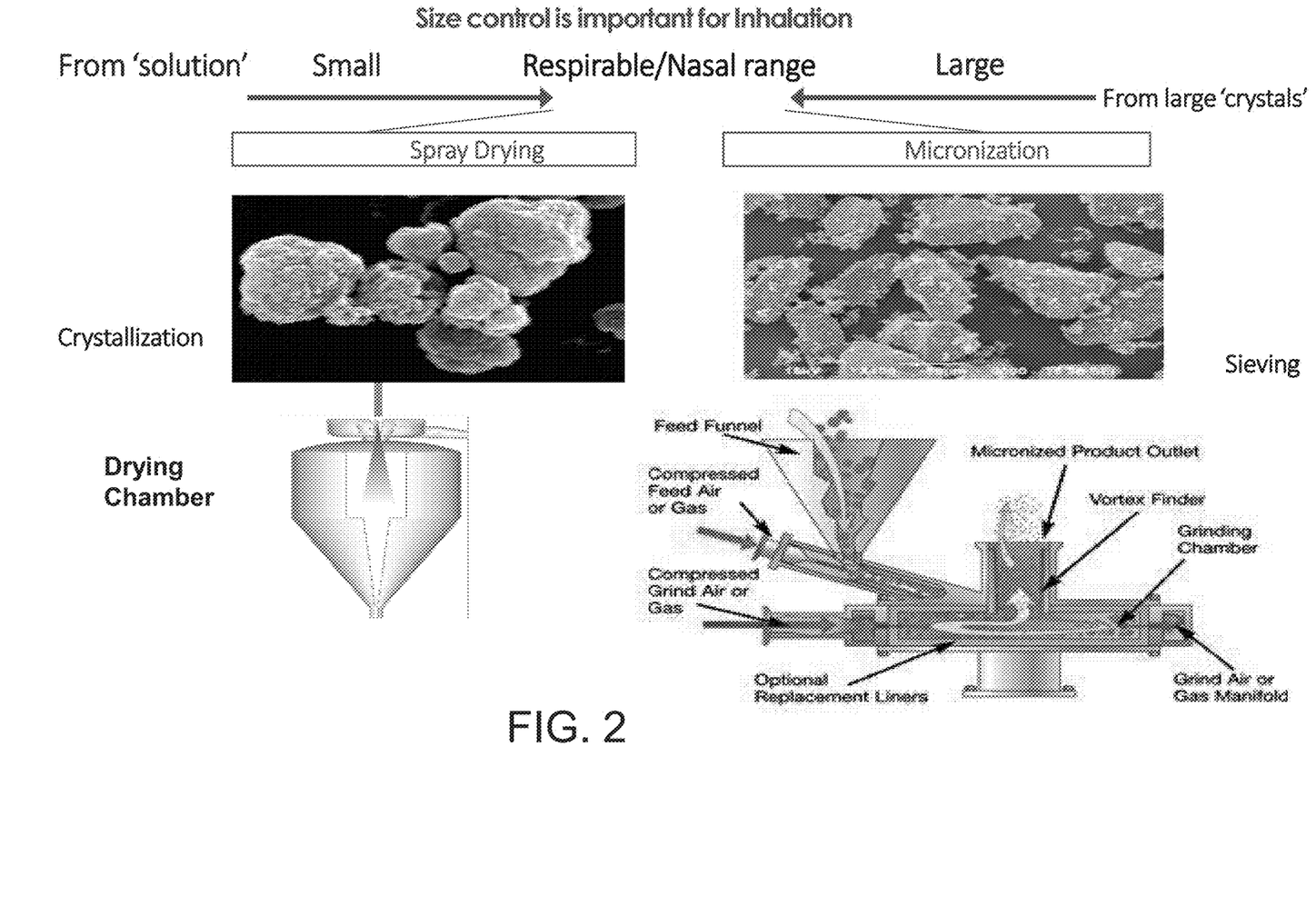
FIG. 2 depicts particle engineering processes of spray drying (from a solution) and micronization (from large crystals) and various conditions to be applied for achieving desired particle size ranges of nanoparticles and microparticles of the compositions of FIG. 1 for inhalation and nasal delivery of the compositions to a human subject, in accordance with embodiments of the present invention.

FIG. 2 depicts particle engineering processes of spray drying (from a solution) and micronization (from large crystals) and various conditions to be applied for achieving desired particle size ranges of nanoparticles and microparticles of the compositions of FIG. 1 for inhalation and nasal delivery of the compositions to a human subject, in accordance with embodiments of the present invention.

For both the spray drying process and the micronization process, niclosamide, hydroxychloroquine, and zinc acetate were solubilized and mixed at equal amounts and formulated in β-cyclodextrin (CD)/chitosan, with added excipients of lactose and/or polyethylene glycol (PEG), to form particles dissolved in a solution.

For spray drying process, the solution was spray dried in a drying chamber, leaving the particles in the form of dry particles of the nanoparticles and the microparticles of the antiviral compositions.

For the micronization process, the particles in the solution were precipitated out of the solution to form crystals. The crystals were fed through a feed funnel and mixed with both feed air or gas and compressed grind air or gas, and then micronized by being mixed with grind air or gas manifold and then ground in a grinding chamber and then fed through a vortex feeder, to complete the micronization process, resulting in the nanoparticles and the microparticles of the antiviral compositions.

Micronization of individual API and spray drying using lactose or pullulan trehalose may be implemented with or without the composite (e.g., cyclodextrin, chitosan and/or PEG) encapsulating the one or more anti-viral compounds and/or at least one cryoprotectant sugar and/or at least one stabilizer.

The nanoparticles and microparticles had sizes ranging from 0.5-5 µm for lung delivery and from 10-50 µm for nasal delivery using a nasal spray. The ratios of the excipient (e.g., PEG and/or lactose) to Active Pharmaceutical Ingredient (API) (e.g., hydroxychloroquine, niclosamide, and/or favipiravir, and zinc salt (e.g., zinc acetate) vary depending upon micronization and/or spray drying processes and the particle size ranges required for pulmonary versus nasal delivery.

Figure 3:
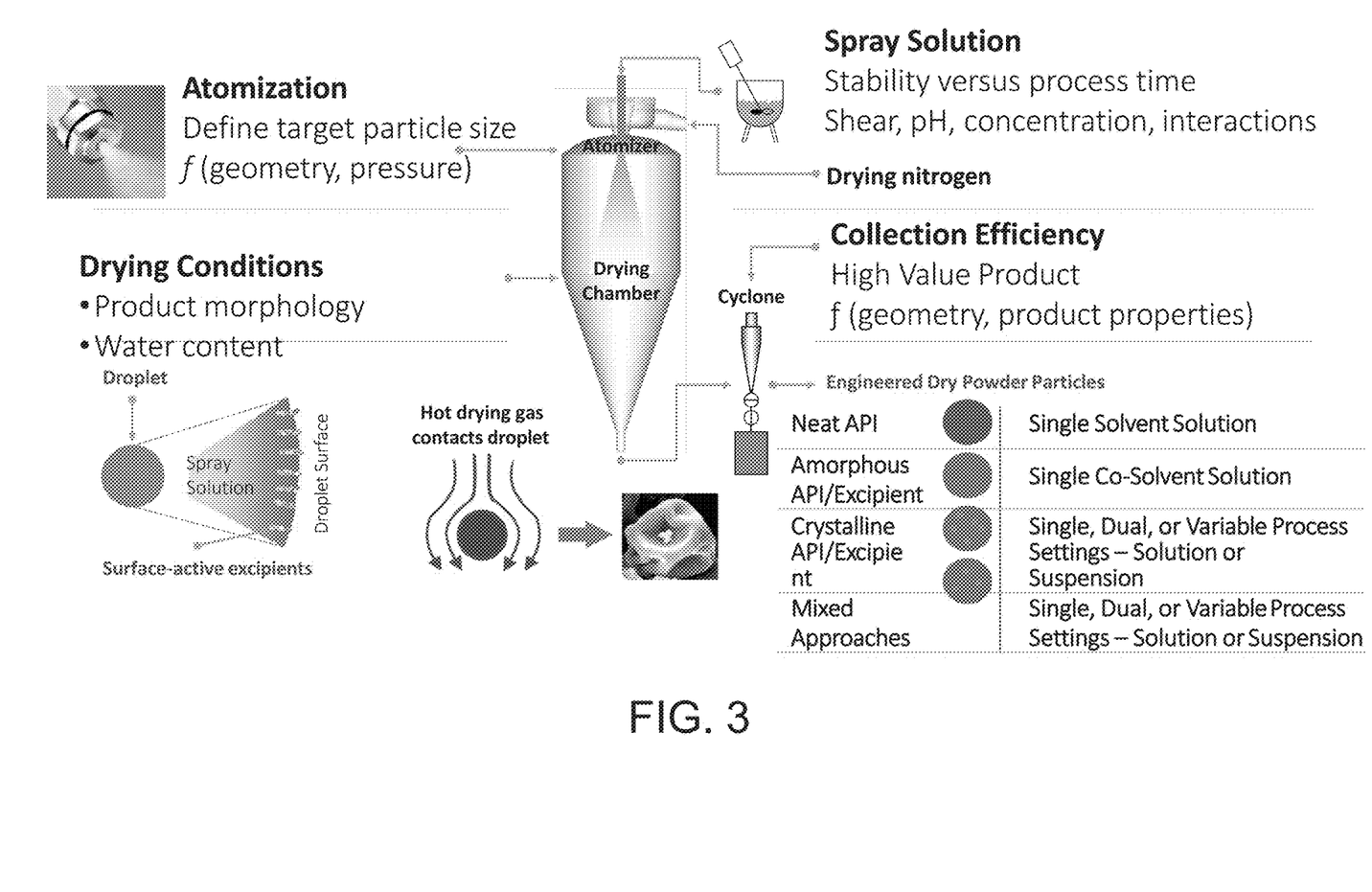
FIG. 3 depict the spray drying process of FIG. 2 in more detail, showing conditions to be applied in achieving the desired dry particle (i.e., nanoparticle and microparticle) size ranges and characteristics for inhalation and nasal delivery of the different compositions to a human subject, in accordance with embodiments of the present invention.

FIG. 3 depict the spray drying process of FIG. 2 in more detail, showing conditions to be applied in achieving the desired dry particle (i.e., nanoparticle and microparticle) size ranges and characteristics for inhalation and nasal delivery of the different compositions to a human subject, in accordance with embodiments of the present invention. A stability of the starting solution versus time is dependent upon, inter alia, shear that the particles in solution are subjected to, pH of the solution, concentration of the particles in the solution, and interactions among the particles in solution.

The resulting dry particle sizes are controlled by the particle geometry and the gas pressure inside the drying chamber in which hot drying gas (e.g., nitrogen gas in one embodiment) in a temperature range of 400° F. to 1000° F. contacts droplets precipitating out of the solution. Surface active excipients may be distributed on the droplet outer surface. The efficiency of collecting the dry particles id dependent upon, inter alia, particle geometry and properties of the product containing the particles.

The dry powder particles and associated solution may include one or more of the following types: neat API (single solvent solution), amorphous API/excipient (single co-solvent solution), crystalline API/excipient (single, dual, or variable process settings—solution or suspension), and mixed approaches (single, dual, or variable process settings—solution or suspension).

For larger size microparticles having particle diameter in a range of 10-100 µm, the ratio of the excipients (PEG and/or lactose) to API (niclosamide, hydroxychloroquine and zinc acetate) was 10/1 in comparison to a 1/1 ratio for the nanoparticles.

Process and material characterization of spray dried nanocrystal or spray-layer suspension onto multi-particulates for encapsulation uses techniques of nano milling, spray drying, and dissolution into suspension. The preceding techniques enable a unit dose of the API in a range of 1-10 mg for niclosamide, hydroxychloroquine, and zinc acetate.

The nano milling is characterized by: Resodyn LabRAM acoustic wet mill or Dyno®-Mill KDL wet mill; and Zirconia spheres as milling media. The formulation includes API, a stabilizing surfactant, and a stabilizing polymer, and 300 nm crystals are formed.

The spray drying is characterized by: Bend Research BLD-35 (up to 250 g), PSD-1 (up to 40 kg), or PSD-2 (up to 400+kg); aqueous spray drying to limit API dissolution; and spraying with bulking agent to improve dispersion of nanocrystals. Niclosamide may be wet milled for increased surface area solubility in aqueous solution.

The dissolution into suspension is characterized by suspension solution may contain viscosity modifying polymer and/or stabilizing surfactant. Primary nanocrystal size is achieved with minimum mixing agitation and good stability.

Optimization of nanocrystal solubility/dissolution for an aqueous spray-drying application is achieved using wet-milling of niclosamide. The wet-milling scaled up enough for aqueous spray-drying, including the other components and any excipients in aqueous solution and the subsequent solid fry powders formation. The generated dry powders showed physical and chemical stability for the solid dry powder inhalers (SDIs) and the liquid form of the dry powders.

Characterization of the SDIs includes appearance, morphology, and particle size by scanning electron microscope (SEM), aerodynamic performance testing through fast impactor, physical state evaluation at different humidity and temperature, and crystallinity by X-ray Powder Diffraction (XRD).

The encapsulation efficiency and loading capacity of niclosamide into niclosamide, hydroxychloroquine/HP-β-Cyclodextrin/chitosan/zinc nano to microparticles was determined by analyzing centrifuged nanoparticles compared to the initial amount of niclosamide. Separation was performed using a flow of rate of 1 mL/minute of methanol:water/ACN (95/5). The elution was monitored at 333-346 nm and injection volume was 101 µL. The amount of niclosamide was determined at 333-346 nm using HPLC and results show that niclosamide encapsulation efficiency was 90%, and niclosamide loading capacity was 10.0%. Hydroxychloroquine was monitored at 255 nm at pH7.4

Analytical methodology for characterization of a product profile of the dry powder of generated microparticles of niclosamide/hydroxychloroquine/zinc acetate includes: imaging (optical microscopy, scanning electron microscopy (SEM)), particle size, aerosol, performance, hygroscopicity (Dynamic Vapor Sorption (DVS), Karl Fischer (KF)), and thermal (Modulated Differential Scanning Calorimetry (mDSC), X-ray Powder Diffraction, Iso-thermal calorimetry (TAM)).

Table 1 shows characteristics of heparins, hydroxychloroquine, favipiravir, and zinc salt into chitosan acetate for Nano-Micro-particle formulations by spray drying and micronization.

TABLE 1

| Active Pharmaceutical Ingredients | Excipients | Size (µm); Zeta potential (mv ± SD) | Methods/ Application |
|---|---|---|---|
| Heparins; Hydroxychloroquine; Niclosamide, Favipiravir; Zinc salt; Corticosteroids | Chitosan, Lactose and/or trehalose | 0.3-1.0 µm. 0-5 mv | Mouth Mist/ Buccal |
| | Chitosan, PEG (2KD), Lactose and/or trehalose | 1-10 µm. 0-5 mv | Inhalation |
| | Chitosan, PEG (10KD), Lactose and/or trehalose | 10-100 µm. 0-5 mv | Nasal |

Dry Powder Inhalers (DPIs) are particularly attractive for delivery of drugs used in the treatment of respiratory diseases, such as asthma, chronic obstructive pulmonary diseases, and cystic fibrosis (Lechanteur A and Evrard B., Influence of Composition and Spray-Drying Process Parameters on Carrier-Free DPI Properties and Behaviors in the Lung: A review, Pharmaceutics 2020, 12, 55; doi:10.3390/pharmaceutics12010055).

Formulation characteristics are critically important for the overall performance of dry powder-based inhalable formulations. The physicochemical properties of both drugs and carriers have important effects on the fluidization, dispersion, delivery, and deposition of the formulations in the airways. Particle size, shape, surface area, and morphology affect the interparticle forces of interaction and aerodynamic properties of the formulations.

Metered-dose inhalers (MDIs) are devices that deliver a specific quantity of drug to the lungs. The size and shape of the micronized drug greatly influence the deposition profile in the lungs of the patient. Although the compendial tests for MDIs are based on cascade impactors, microscopic analysis is recommended by regulatory guidance documents and delivers important information. Automated image analysis now facilitates quantitative particle size and shape distribution data that can prove valuable to both formulators and quality control efforts.

An MDI typically delivers a specific dose of a micronized drug by supplying a short burst of aerosolized medicine that is inhaled by the patient. The medicine is commonly used to treat respiratory diseases such as asthma or chronic obstructive pulmonary disease (COPD). The medicine in a metered dose inhaler is most commonly a bronchodilator, corticosteroid, or a combination of a bronchodilator and a corticosteroid.

The present invention provides a composition, comprising heparin, LMWH or S-NACH in combination with low dose corticosteroid and/or hydroxychloroquine along with zinc salt in dry Powder Inhalers (DPIs) or carrier based aerosolized inhaler with HFA. DPIs are particularly attractive for delivery of drugs used in the treatment of respiratory diseases, such as asthma, chronic obstructive pulmonary diseases, and infectious diseases.

Formulation characteristics are important for the overall performance of dry powder-based inhalable formulations. The physicochemical properties of both drugs and carriers have important effects on the fluidization, dispersion, delivery, and deposition of the formulations in the airways. Particle size, shape, surface area, and morphology affect the interparticle forces of interaction and aerodynamic properties of the formulations.

Sugars, such as trehalose and raffinose may employed to act as protein or large molecular weight stabilizers. Optimization of the aerodynamic characteristics of microparticles in dry powder inhaler formulations ensures optimum deposition of the formulation into the respiratory tract. Trehalose and the trisaccharide, raffinose, of a previously reported spray drying process may be used for producing nanoporous microparticles (NPMPs) (Lan, L.; Xu, D.; Ye, G.; Xia, C; Wang, S.; Li, Y.; Xu, H., Positive RT-PCR Test Results in Patients Recovered From COVID-19, JAMA. 2020 Feb. 27. doi: 10.1001/jama.2020.2783).

While spray drying raffinose or trehalose from aqueous solution or ethanol:water solutions resulted in non-porous microspheres, spray drying from a methanol:n-butyl acetate mixed solvent system resulted in microparticles which appeared to consist of an agglomeration of individual nanoparticles; i.e., nano-porous/nanoparticles—microparticles. NPMPs of trehalose and raffinose were amorphous, with glass transition temperatures. NPMPs demonstrated improved aerosolization properties compared to spray dried non-porous particles.

Heparin or LMWH, S-NACH was mixed with lactose or trehalose according to a ratio of 1:3, 1:5, and 1:10. The resulting solution was spray dried using spray dryer D10 and D90. The final formulation contained 100-20,000 USP U Heparin or LMWH per 1-200 mg of powder.

In one embodiment, the heparin daily dose may be in a range of 10-200 mg, the corticosteroid (e.g., dexamethasone or betamethasone) daily dose may be 0.1-0.5 mg, the hydroxychloroquine daily dose may 1-100 mg (e.g., 10 mg), and the zinc salt daily dose may be in a range of 10-50 mg (e.g., 10 mg).

Different modes of inhalation delivery that can be used include: (a) a nebulizer employing nebulization by air-jet, using vibrating mesh technology producing aerosol droplets generated from liquids; (b) an aerosolized inhaler such as a pressurized metered dose inhaler (PMDI) which uses a propellant for propelling aerosol droplets generated from a drug suspension in volatile liquid; and (c) dry powder inhaler (DPI) characterized by high stability and sterility using small portable devices.

The present invention provides a composition, comprising: microparticles and/or nanoparticles, wherein a pharmaceutically active agent, corticosteroid and/or hydroxychloroquine and/or niclosamide and/or favipiravir, and a zinc salt are incorporated in the microparticles and/or nanoparticles, and wherein the pharmaceutically active agent is selected from the group consisting of unfractionated heparin (UFH), Low Molecular Weight Heparin (LMWH), sulfated non-anticoagulant heparin (S-NACH), other glycosaminoglycans (GAGs), and combinations thereof.

In one embodiment, the composition comprises 10,000-40,000 IU of the pharmaceutically active agent.

In one embodiment, the composition comprises 0.1-0.5 mg of the corticosteroid.

In one embodiment, the composition comprises 10-30 mg of the hydroxychloroquine.

In one embodiment, the composition comprises 10-30 mg of the niclosamide.

In one embodiment, the composition comprises 10-30 mg of the favipiravir.

In one embodiment, the composition comprises 10-30 mg of the hydroxychloroquine in a form of hydroxychloroquine sulfate.

In one embodiment, the composition comprises 10-30 mg of the zinc salt.

In one embodiment, the composition comprises the 10-100 mg of the hydroxychloroquine.

In one embodiment, a hydrofluoroalkane (HFA) propellant is incorporated in the microparticles and/or nanoparticles, and wherein the composition comprises a liquid selected from the group consisting of a solution that includes a solvent in which the microparticles and/or nanoparticles are dissolved and a suspension in which the microparticles and/or nanoparticles are suspended.

In one embodiment, the liquid is within a metered-dose inhaler (MDI), a nasal spray, or a nebulizer. A therapeutic dose of the composition may be delivered to the subject (i.e., mammal such as human being) using the nasal spray.

In one embodiment, the liquid is the suspension.

In one embodiment, the solution comprises chitosan acetate (2,000-10,000 Dalton) n an amount which substantially enhances a solubility of the pharmaceutically active agent in the liquid.

In one embodiment, the composition comprises ethanol in an amount which does not substantially enhance a solubility of the pharmaceutically active agent in the liquid.

In one embodiment, the ethanol is less than 1% by weight of the liquid.

In one embodiment, the HFA propellant comprises HFA 227, HFA 134a, or a combination thereof.

In one embodiment, the liquid is the solution.

In one embodiment, the solution comprises chitosan acetate in an amount (e.g., 2,000-10,000 Dalton) which substantially enhances a solubility of the pharmaceutically active agent in the liquid.

In one embodiment, the solvent is water or buffered saline.

In one embodiment, the microparticles and/or nanoparticles comprise a vinyl polymer.

In one embodiment, vinyl polymer is polyvinylpyrrolidone.

In one embodiment, the microparticles and/or nanoparticles are configured as a dry powder.

In one embodiment, the dry powder is within a dry powder inhaler (DPI).

In one embodiment, the zinc salt comprises zinc acetate.

In one embodiment, the microparticles are coated with 0.1-10 μm of lactose, mannitol, trehalose, or combinations thereof.

In one embodiment, the microparticles and/or nanoparticles are coated with 10-100 μm of lactose, mannitol, trehalose, or combination thereof.

In one embodiment, the microparticles and/or nanoparticles comprise surfactants, lubricants, flavoring agents, additives, or combinations thereof.

The present invention provides a method for treating a mammal infected with a virus. The method includes administering a therapeutic dose of the composition to a mammal. In one embodiment, the mammal is a human being.

In one embodiment, the virus is selected from the group consisting of dengue fever viruses, SARS corona viruses, Chikungunya viruses, enteroviruses, influenza viruses, herpes simplex viruses, Coronavirus (COVID-19), other viruses, and combinations thereof.

In one embodiment, the mammal to which the therapeutic dose of the composition has been administered is less capable of entering a living mammalian cell of the mammal and/or undergoing replication within the living mammalian cell as compared with the virus had the therapeutic dose of the composition not been administered to the mammal.

The present invention provides an inhalation delivery system for prevention and treatment of upper respiratory tract viruses. The inhalation delivery system includes an apparatus configured to deliver a therapeutic dose of the composition to a mammal (e.g., a human being) via inhalation delivery.

In one embodiment, the apparatus comprises a dry powder inhaler (DPI) characterized by high stability and sterility using small portable devices.

In one embodiment, the apparatus comprises a nebulizer employing nebulization by air-jet, using vibrating mesh technology producing aerosol droplets generated from liquids.

In one embodiment, the apparatus comprises a pressurized metered dose inhaler (PMDI) which uses a propellant for propelling aerosol droplets generated from a drug suspension in a volatile liquid.

In one embodiment, the apparatus comprises a nasal spray, and wherein the therapeutic dose of the composition is delivered to the mammal using the nasal spray.

In one embodiment, the apparatus comprises a mouth mist spray, wherein the therapeutic dose of the composition is delivered to the mammal via mouth or buccal cavity using the mouth mist spray.

Spray-drying of a combination of molecules, to enable delivery by inhalation to the lung for COVID-related indications, may be used to counter upper respiratory tract and systemic complications. Micronized and/or spray dry powder filled in capsule may be used for DPI and aerosolized inhalation delivery.

Micronized or spray dried powder, including hydroxychloroquine, heparin nanocrystal, favipiravir and micronized zinc salt (acetate or glucoronate), may be encapsulated in chitosan acetate with lactose, mannitol and/or trehalose or combination thereof.

Micronized or spray dried powder, including hydroxychloroquine, heparin nanocrystal, favipiravir and micronized zinc salt (acetate or glucoronate) with added unfractionated heparin or Low Molecular Weight Heparin (LMWH), may be encapsulated in chitosan acetate with lactose, mannitol and/or trehalose or combination thereof.

Micronized or spray dried powder may include hydroxychloroquine, haparin, and a zinc salt may be encapsulated in chitosan acetate with lactose, mannitol and/or trehalose.

Nanocrystals may be formed using wet-milling of heparain to optimize the nanocrystal solubility/dissolution for an aqueous spray-drying application. Wet-milled nanocrystals may be scaled up enough for aqueous spray-drying, including other pharmaceutically active components and any excipients in aqueous solution and the subsequent solid powders formation. The generated powders showed physical and chemical stability for the solid dry powder inhalers (SDIs) and a liquid form of the generated powders.

Characterization of the SDIs include: appearance, morphology and particle size by scanning electron microscopy (SEM), aerodynamic performance testing through fast impactor, physical state evaluation at different humidity and temperature, and crystallinity by X-ray Powder Diffraction (XRD).

Chemical and physical characterization pertaining to use of a DPI include solubility profiles in HFA propellants and co-solvents, salt selection, excipient compatibility, chemical stability evaluation, and degradation pathway identification.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising:
   microparticles and/or nanoparticles, wherein the microparticles and/or nanoparticles comprise a first pharmaceutically active agent and a second pharmaceutically active agent, wherein the first pharmaceutically active agent comprises unfractionated heparin (UFH), Low Molecular Weight Heparin (LMWH), sulfated non-anticoagulant heparin (S-NACH) or a combination thereof, and wherein the second pharmaceutically active agent comprises 10-30 mg of hydroxychloroquine in a form of hydroxychloroquine sulfate, 10-30 mg of favipiravir, or a combination thereof.

2. The composition of claim 1, wherein the microparticles and/or nanoparticles further comprise 10-30 mg of a zinc salt.

3. The composition of claim 1, wherein the microparticles and/or nanoparticles further comprise niclosamide.

4. The composition of claim 1, wherein the microparticles and/or nanoparticles further comprise one or more corticosteroids.

5. The composition of claim 4, wherein the one or more corticosteroids are present in the microparticles and/or nanoparticles in an amount of 0.1-0.5 mg, and wherein the one or more corticosteroids comprise dexamethasone, betamethasone, or a combination thereof.

6. The composition of claim 1, wherein the microparticles and/or nanoparticles further comprise a hydrofluoroalkane (HFA) propellant, and wherein the composition comprises a liquid selected from the group consisting of a solution that includes a solvent in which the microparticle s and/or nanoparticles are dissolved and a suspension in which the microparticles and/or nanoparticles are suspended.

7. The composition of claim 6, wherein the liquid is within a metered-dose inhaler (MDI), a nasal spray, or a nebulizer.

8. The composition of claim 6, wherein the liquid is the suspension.

9. The composition of claim 6, wherein the liquid is the solution.

10. The composition of claim 9, wherein the solution comprises chitosan acetate in an amount which substantially enhances a solubility of the pharmaceutically active agent in the liquid.

11. The composition of claim 9, wherein the solvent is water or buffered saline.

12. The composition of claim 6, wherein the HFA propellant comprises HFA 227, HFA 134a, or a combination thereof.

13. The composition of claim 1, wherein the microparticles and/or nanoparticles further comprise a vinyl polymer.

14. The composition of claim 13, wherein the vinyl polymer is polyvinylpyrrolidone.

15. The composition of claim 1, wherein the microparticles and/or nanoparticles are configured as a dry powder.

16. The composition of claim 15, wherein dry powder is within a dry powder inhaler (DPI).

17. The composition of claim 1, wherein the microparticles and/or nanoparticles are coated with 0.1-10 μm of lactose, mannitol, or trehalose.

18. The composition of claim 1, wherein the microparticles and/or nanoparticles are coated with 10-100 m of lactose, mannitol, or trehalose.

19. The composition of claim 2, wherein the zinc salt comprises zinc acetate.

20. The composition of claim 1, wherein the microparticles and/or nanoparticles further comprise surfactants, lubricants, flavoring agents, additives, or combinations thereof.

21. A method for treating a mammal infected with a virus, said method comprising:
administering a therapeutic dose of a composition to the mammal, wherein the composition comprises microparticles and/or nanoparticles, wherein the microparticles and/or nanoparticles comprise a first pharmaceutically active agent and a second pharmaceutically active agent, wherein the first pharmaceutically active agent comprises unfractionated heparin (UFH), Low Molecular Weight Heparin (LMWH), sulfated non-anticoagulant heparin (S-NACH) or a combination thereof, and wherein the second pharmaceutically active agent comprises 10-30 mg of hydroxychloroquine in a form of hydroxychloroquine sulfate, 10-30 mg of favipiravir, or a combination thereof.

22. The method of claim 21, wherein the mammal is a human being.

23. The method of claim 21, wherein the virus is selected from the group consisting of dengue fever viruses, SARS corona viruses, Chikungunya viruses, enteroviruses, influenza viruses, herpes simplex viruses, Coronavirus, other viruses, and combinations thereof.

24. The method of claim 21, wherein the virus in the mammal to which the therapeutic dose of the composition has been administered is less capable of entering a living mammalian cell of the mammal and/or undergoing replication within the living mammalian cell as compared with the virus had the therapeutic dose of the composition not been administered to the mammal.

25. An inhalation delivery system for prevention and treatment of upper respiratory tract viruses, said inhalation delivery system comprising a composition and an apparatus configured to deliver a therapeutic dose of the composition to a mammal via inhalation delivery, wherein the composition comprises microparticles and/or nanoparticles, wherein the microparticles and/or nanoparticles comprise a first pharmaceutically active agent and a second pharmaceutically active agent, wherein the first pharmaceutically active agent comprises unfractionated heparin (UFH), Low Molecular Weight Heparin (LMWH), sulfated non-anticoagulant heparin (S-NACH) or a combination thereof, and wherein the second pharmaceutically active agent comprises 10-30 mg of hydroxychloroquine in a form of hydroxychloroquine sulfate, 10-30 mg of favipiravir, or a combination thereof.

26. The inhalation delivery system of claim 25, wherein the apparatus comprises a dry powder inhaler (DPI) characterized by high stability and sterility using small portable devices.

27. The inhalation delivery system of claim 25, wherein the apparatus comprises a nebulizer employing nebulization by air-jet, using vibrating mesh technology producing aerosol droplets generated from liquids.

28. The inhalation delivery system of claim 25, wherein the apparatus comprises a pressurized metered dose inhaler (PMDI) which uses a propellant for propelling aerosol droplets generated from a drug suspension in a volatile liquid.

29. The inhalation delivery system of claim 25, wherein the apparatus comprises a nasal spray, and wherein the therapeutic dose of the composition is delivered to the mammal using the nasal spray.

30. The inhalation delivery system of claim 25, wherein the apparatus comprises a mouth mist spray, and wherein the therapeutic dose of the composition is delivered to the mammal via mouth or buccal cavity using the mouth mist spray.

* * * * *